(12) United States Patent
Smith

(10) Patent No.: US 7,125,509 B1
(45) Date of Patent: Oct. 24, 2006

(54) APPARATUS AND METHOD FOR PRESCRIBING AND MANUFACTURING ORTHOTIC FOOT DEVICES

(76) Inventor: Neil Robert Smith, 19 Charles Street, Petersham, NSW 2061 (AU)

( * ) Notice: Subject to any disclaimer, the term of this patent is extended or adjusted under 35 U.S.C. 154(b) by 263 days.

(21) Appl. No.: 10/070,992

(22) PCT Filed: Sep. 13, 2000

(86) PCT No.: PCT/AU00/01107

§ 371 (c)(1),
(2), (4) Date: Jul. 17, 2002

(87) PCT Pub. No.: WO01/19246

PCT Pub. Date: Mar. 22, 2001

(30) Foreign Application Priority Data

Sep. 14, 1999 (AU) .................................... PQ2844

(51) Int. Cl.
*A61B 5/103* (2006.01)
*B29C 33/38* (2006.01)

(52) U.S. Cl. ............... 264/223; 12/146 B; 33/515; 425/2; 600/592

(58) Field of Classification Search ............... 264/222, 264/223; 425/2; 12/146 B; 33/515; 600/592
See application file for complete search history.

(56) References Cited

U.S. PATENT DOCUMENTS

| | | | |
|---|---|---|---|
| 4,062,355 A * | 12/1977 | Kaye ........................... | 600/592 |
| 4,492,236 A | 1/1985 | Pile | |
| 4,662,079 A * | 5/1987 | Graf et al. ..................... | 33/512 |
| 4,747,989 A | 5/1988 | Peterson | |
| 4,802,494 A | 2/1989 | Gardiner | |
| 5,088,503 A | 2/1992 | Seitz | |
| 5,282,328 A | 2/1994 | Peterson | |
| 5,928,673 A | 7/1999 | Ryan et al. | |
| 5,979,067 A * | 11/1999 | Waters ......................... | 33/512 |
| 6,170,177 B1 * | 1/2001 | Frappier et al. .......... | 12/142 R |
| 6,782,630 B1 * | 8/2004 | Root ............................ | 33/515 |

FOREIGN PATENT DOCUMENTS

GB         2312754         11/1997

* cited by examiner

*Primary Examiner*—Allan R. Kuhns
(74) *Attorney, Agent, or Firm*—Arent Fox PLLC

(57) ABSTRACT

The present invention discloses an apparatus which enables in-situ casts of the feet of a patient to be made whilst the feet support the patient's weight. In particular, two heel supports (28, 29) and two stirrups (38, 39) receive the heels and forefeet of the patient. Each is capable of independent movement being both rotation about the heel-toe axis and movement substantially transverse to that axis. A method of forming a cast of the patient's feet is also disclosed.

16 Claims, 6 Drawing Sheets

APPARATUS AND METHOD FOR PRESCRIBING AND MANUFACTURING ORTHOTIC FOOT DEVICES

FIELD OF THE INVENTION

The present invention relates to the prescription and manufacture of orthotic devices for the feet and, in particular, relates to an apparatus and method for taking a corrective weight bearing cast and measurement of a patient's feet in order to form a corrective orthotic foot device such as an orthotic inner sole.

BACKGROUND TO THE INVENTION

The present invention discloses an apparatus which makes the process of the prescription and manufacture of custom-made orthotic devices for the feet simpler, less expensive and more accurate. Orthoses for the feet are inner sole devices which are inserted into a person's shoes to correct malalignment of the foot, which can cause a variety of physical symptoms, including lower back pain, knee and other joint problems, heel spurs and general foot pain.

Orthotic therapy is defined as the use of an appliance or apparatus to support, align, prevent or correct deformity, or to modify position or motion, and improve the function of the movable parts of the body. The "orthoses" is the actual appliance or device. Orthotic foot devices are the most common form of orthoses and are generally used to correct malalignment of the feet. The device is inserted into the shoe and corrects, or attempts to correct, the malalignment by tilting the foot into its proper position.

Malalignment of the foot will usually mean that the foot leans too much to one side when standing or walking. This can cause symptoms such as back pain, knee problems and leg or general foot pain. The symptoms can be aggravated by age or sporting activities and it is usually only after a person has suffered ongoing chronic pain in their back, leg, knees or feet that the person will seek help. Diabetic patients over 60 years of age generally benefit greatly from feet orthoses. Correctly prescribed, foot orthoses can spread pressure evenly over the foot base and thus reduce the incidence of chronic ulcers.

In some cases, patients will visit a podiatrist to request orthoses after prior consultation with other medical and paramedical practitioners—such as physiotherapists, chiropractors or osteopaths—for a condition they would not have normally associated with the foot. In other cases, the patient will be prescribed orthotic inserts after consulting a podiatrist about general foot or heel pain. In most other instances, the patient will have heard of the benefits of orthotic inserts from satisfied former patients. Orthotic devices are popular with both professional and keen amateur sports people through word of mouth and also through the growth in the number of doctors specialising in sports medicine.

Pre-fabricated, generically sized, orthotic devices are also sold over the counter in pharmacies and by mail order by medical suppliers.

Orthotic devices for the feet have been widely prescribed by podiatrists in Australia since the early 1970s. Prior to this, neither podiatrists nor chiropodists were trained in assessing biomechanical abnormalities of the foot, a prerequisite for the prescribing of orthoses. Orthotic therapy has proved successful for many patients and demand has increased, mainly through word of mouth.

PRIOR ART

As described above, orthoses for the feet are generally prescribed by podiatrists, who are university-trained foot specialists, using variations of a common known method. Following the diagnosis that orthoses would assist a patient, a podiatrist will take a cast of each foot using a wet plaster bandage. The foot is held in the air by the podiatrist who attempts to replicate the standing position of the foot, while correctly aligning the sub talor joint so that the foot sits in its correctly aligned position. The podiatrist then writes instructions on the cast and further instructions on the prescription form which are then sent to a laboratory. The laboratory technician will create a positive mould and then hand craft the orthoses using the podiatrist's instructions and their own skill. In such prior art methods it is up to the laboratory technician to guess at how the orthoses should be shaped in order to correct a patient's foot malalignment using the podiatrist's prescription as a guide. This is because the mould taken by the podiatrist is of the patient's feet in an elevated position, not in a standing or "weight bearing" position. The technician must therefore guess at how the corrected weight-bearing morphology of a patient's foot differs from the non weight bearing morphology provided by the cast and adjust the orthoses as he sees fit. As a result, the finished product will be heavily influenced by the technique and level of skill of the technician who is making the orthoses. Accordingly, with such prior art methods of prescribing and manufacturing orthotic foot devices there is significant opportunity for human error at both the casting, prescription and manufacturing stages.

Prior art searches conducted after the priority date disclosed various prior art of general interest. U.K. Patent Application No. GB 2,312,754A (Pearce) discloses a foot plate 1 which is able to be pivoted (only) about the heel-toe axis of the foot. Further each foot is measured in turn (on the one foot plate) rather than measuring both feet simultaneously.

Similarly, U.S. Pat. No. 4,802,494 (Gardiner) discloses apparatus with toe, arch, and heel plates 26, 28 and 30 which are each independently rotatable. There is no independent translation of the heel plate 30 transverse to the heel-toe axis of the foot. A similar comment applies in respect of the heel support platform 346.

Another prior art specification is U.S. Pat. No. 4,492,236 (Pile) which again discloses heel plates 306, 310 and sole plates 308, 312 which are each able to spherically pivot about a vertical axis movable longitudinally relative to the heel-toe axis of the foot. U.S. Pat. No. 5,928,673 (Ryan) discloses a calliper arrangement for holding the patient's leg in order to take a mould, but without any pivotable or translatable foot supports.

OBJECT OF THE INVENTION

Accordingly, the object of the present invention is to provide an apparatus and method for prescribing and manufacturing orthotic foot devices which improve on the prior art arrangements.

SUMMARY OF THE INVENTION

According to a first aspect of the present invention there is disclosed apparatus to correctly align a foot to permit an orthotic device to be fabricated, said apparatus comprising:— a heel support and a front foot rest positioned substantially level therewith and in front of the heel support to thereby define a heel-toe axis said heel support being mounted on a heel adjustment means arranged to simultaneously pivot said heel support about said heel-toe axis and move said heel support transverse to said heel-toe axis.

In accordance with a second aspect of the present invention there is disclosed a method of casting a mould of a compensated foot whilst a patient's weight is carried by the foot, said method comprising the steps of:—
(a) standing the patient on a pair of spaced apart heel supports whilst supporting the front of the patient's feet,
(b) adjusting at least the heel supports to compensate for any malalignment of the patient's feet,
(c) lifting one foot free of said heel support and applying a settable casting bandage to said foot,
(d) replacing said one foot on said heel support and, if necessary, repeating said compensation step (b),
(e) maintaining said foot in the compensated configuration until said casting bandage sets, and
(f) removing said one foot from said heel support and slipping said one foot from said set cast.

In accordance with a third aspect of the present invention there is disclosed a method of casting a mould of a compensated foot whilst a patient's weight is carried by the foot, said method comprising the steps of:—
(a) standing the patient on a pair of spaced apart heel supports whilst supporting the front of the patient's feet,
(b) lifting one foot free of said heel support and applying a settable casting bandage to said foot,
(c) replacing said one foot on said heel support,
(d) adjusting at least the heel supports to compensate for any malalignment of the patient's feet,
(e) maintaining said foot in the compensated configuration until said casting bandage sets, and
(f) removing said one foot from said heel support and slipping said one foot from said set cast.

BRIEF DESCRIPTION OF THE DRAWINGS

One embodiment of the present invention will now be described with reference to the drawings in which:—

DETAILED DESCRIPTION

Figure 1:
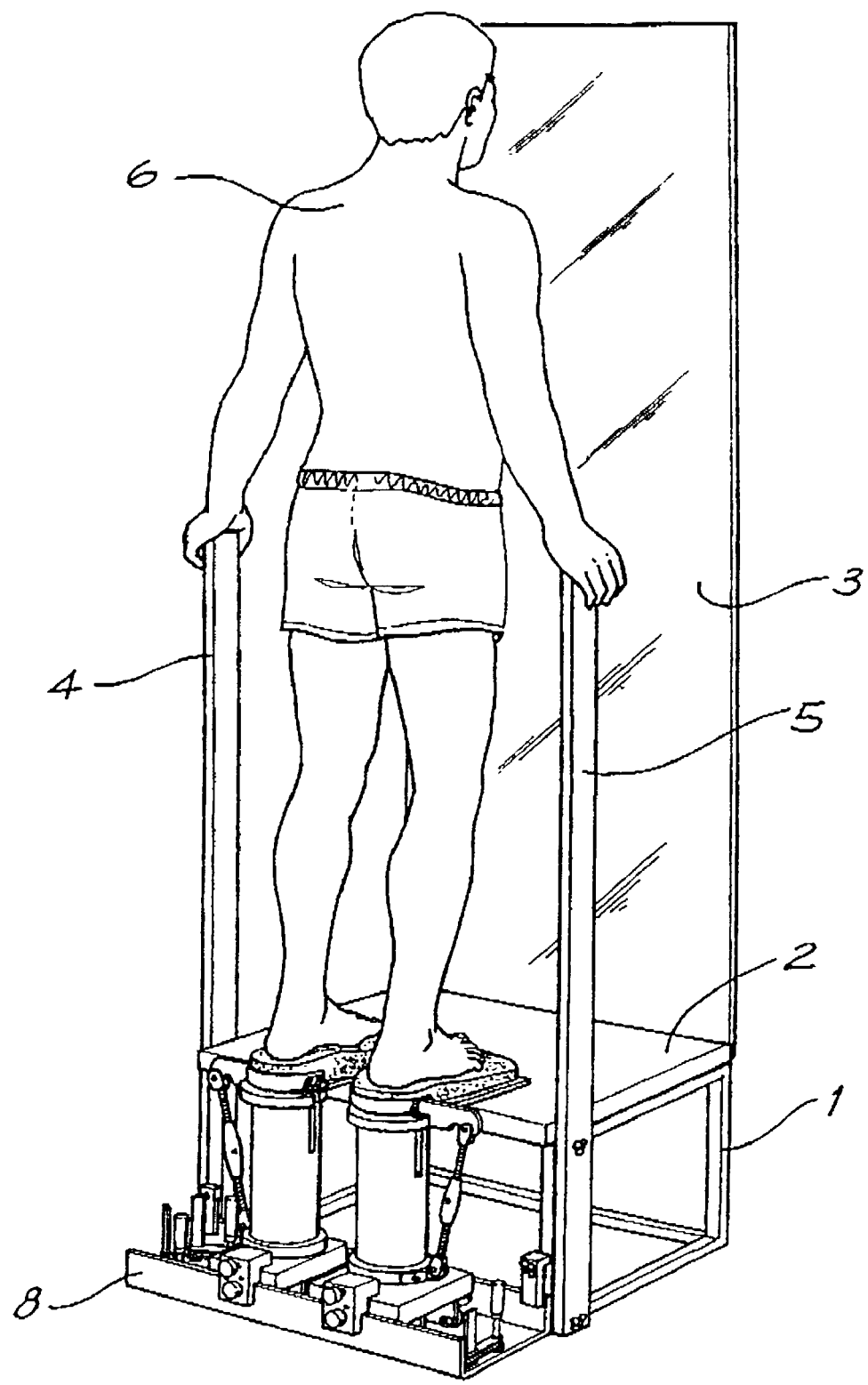
FIG. 1 is a rear perspective view showing a patient standing on the apparatus of the preferred embodiment.

As seen in FIG. 1, the apparatus of the preferred embodiment has a generally rectangular frame 1 which supports a bench top 2 which, as will be explained hereafter, forms a front footrest. Extending upwardly from the bench top 2 is a mirror 3 which is located at the front of the apparatus. Extending upwardly from the frame 1 are a pair of hand rails 4, 5 which extend to a convenient hip height and are able to be grasped by the patient 6.

Figure 2:
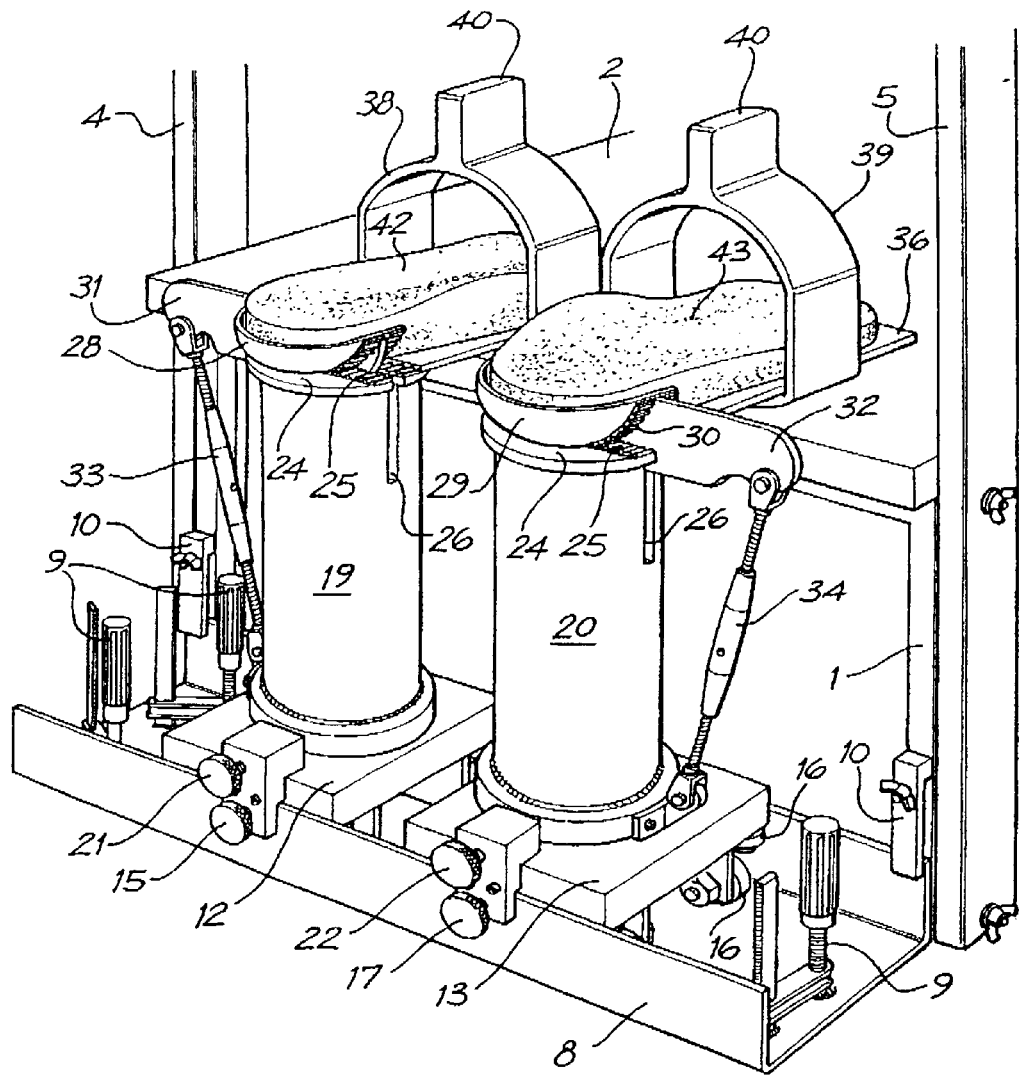
FIG. 2 is a similar rear perspective view showing the detail of the apparatus of FIG. 1.

To the rear of the frame 1 is located the remainder of the apparatus which is illustrated in more detail in FIG. 2. Not illustrated in FIG. 1 is a small bench or stool which enables the patient to conveniently step up from the floor into the position illustrated in FIG. 1 and upon which the podiatrist is able to sit whilst using the apparatus.

Figure 3:
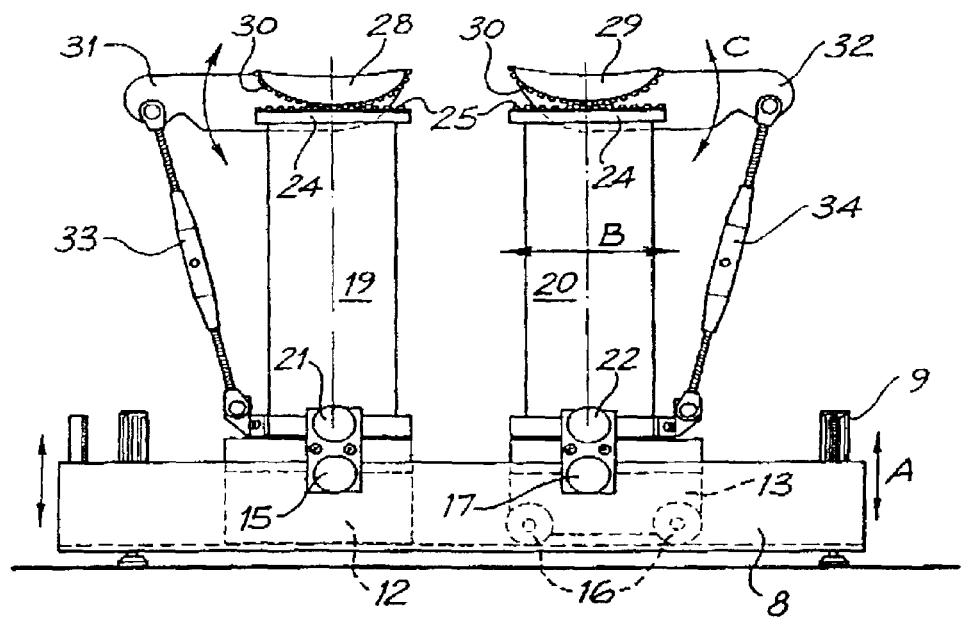
FIG. 3 is a rear elevational view showing the movement of the heel adjustment mechanism.

Turning now to FIGS. 2–5, to the rear of the frame 1 is located a U-channel 8 which is provided with three threaded levelling adjustors 9 which are able to be rotated so as to raise or lower the opposite ends of the U-channel 8 in the direction of arrows A as seen in FIG. 3. This ensures that the base of the U-channel 8 is level, irrespective of any irregularities in the floor surface. Once this levelling activity is undertaken, the U-channel 8 and frame 1 can be clamped together by means of clamps 10 as seen in FIG. 2.

In addition, the adjustors 9 can be used to raise or lower the entire channel 8 to adjust for the height of the heels of the shoes to be worn by the patient. The clamps 10 are then used to fix this adjustment.

Positioned within the U-channel 8 are two bases 12, 13. The left hand base 12 is able to be slid along the U-channel 8 and is secured into its desired position by means of a knurled grub screw 15. The right hand base 13 is provided with wheels 16 which permit it to be easily rolled along the U-channel 8 in the direction of arrows B in FIG. 3. The base 13 can be fixed relative to the U-channel 8 by means of grub screw 17. The above arrangements enable the absolute and relative position of each of the bases 12, 13 to be determined.

Mounted on the bases 12, 13 are corresponding hollow cylindrical supports 19, 20. The supports 19, 20 fit over a cylindrical boss (not illustrated) located on the upper surface of the bases 12, 13 and about which the supports 19, 20 are able to rotate in a vertical axis. A further pair of grub screws 21, 22 secures the supports 19, 20 relative to their corresponding bases 12, 13.

Each of the supports 19, 20 has a corresponding flat upper surface 24 which carries a pair of flat racks 25. A vertically extending slot 26 passes through the upper surface 24 and into the upper portion of the side wall of the supports 19, 20. Positioned above the upper surfaces 24 are two heel supports 28, 29 on the underside of each of which is carried a pair of curved racks 30 which engage with the pair of flat racks 25. The heel supports 28, 29 each have secured to their undersurface a corresponding tilt arm lever 31, 32 to which a turnbuckle 33, 34 is connected.

Figure 4:
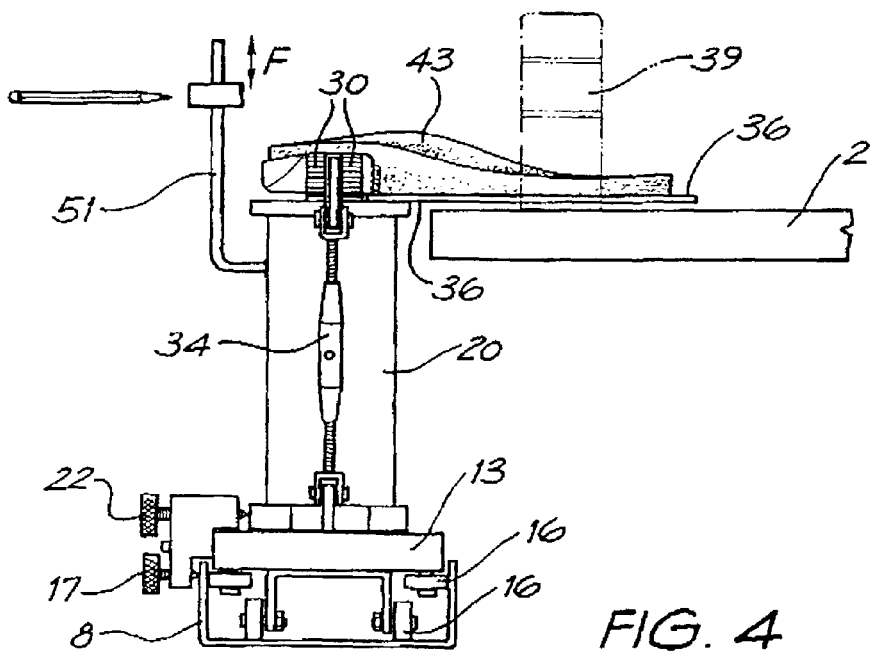
FIG. 4 is a side view of the apparatus showing the relationship between the heel support and the front foot rest.
Figure 5:
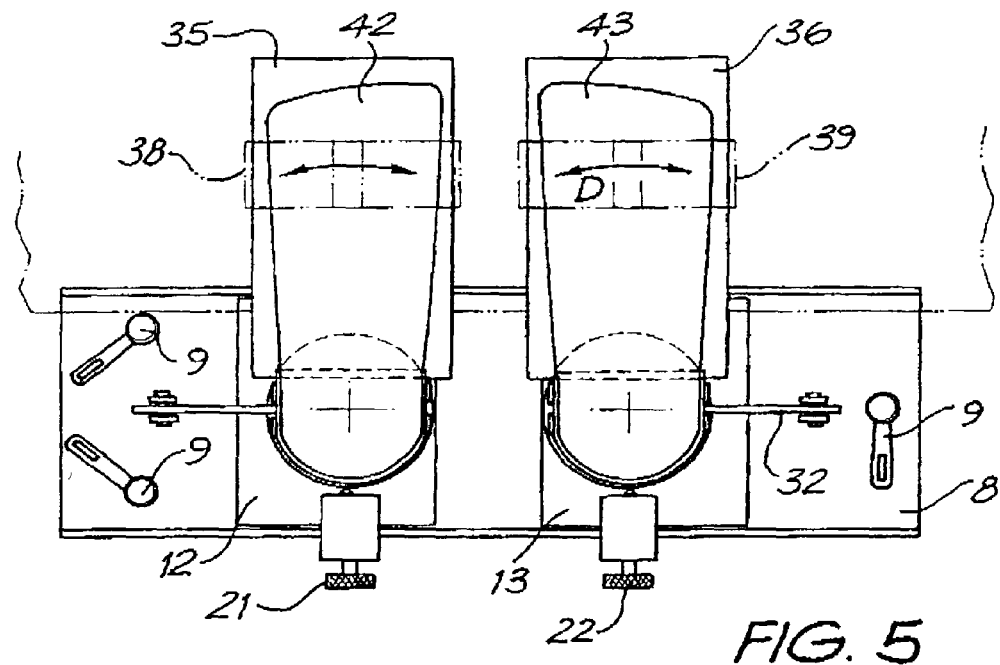
FIG. 5 is a plan view of the apparatus showing the ability of the heel supports to move about a vertical axis.

As best seen in FIGS. 4 and 5, two front foot plates 35, 36 sit on the bench top 2 and extend across the gap between the bench top 2 and the flat surface 24. The thickness of each of the support plates 35, 36 corresponds to the height of the teeth on the flat rack 25.

Located on the front foot plates 35, 36 are corresponding front foot supports in the form of two stirrups 38, 39 each of which is generally tubular in construction and has a vertically extending lug 40 which is able to be conveniently manually grasped. Positioned on the heel supports 28, 29 and the front foot plates 35, 36 are two deformable liners 42, 43 which are shaped to support the patient's corresponding foot including all plantar surfaces (including the instep).

In use, the podiatrist first examines the stance of the patient and utilising the grub screws 15, 17 adjust the position of the bases 12, 13 in the U-channel in order that the spacing between the heel supports 28, 29 correspond to the patient's stance. In addition, as indicated in FIG. 5, by use of the grub screws 21, 22, the supports 19, 20 can be rotated about their vertical axis so as to move the front foot plates 35, 36 in the direction indicated by arrows D in FIG. 5 so as to set the appropriate toe-in or toe-out for the patient. The patient then mounts the apparatus as indicated in FIG. 1 and stands erect.

Figure 6:
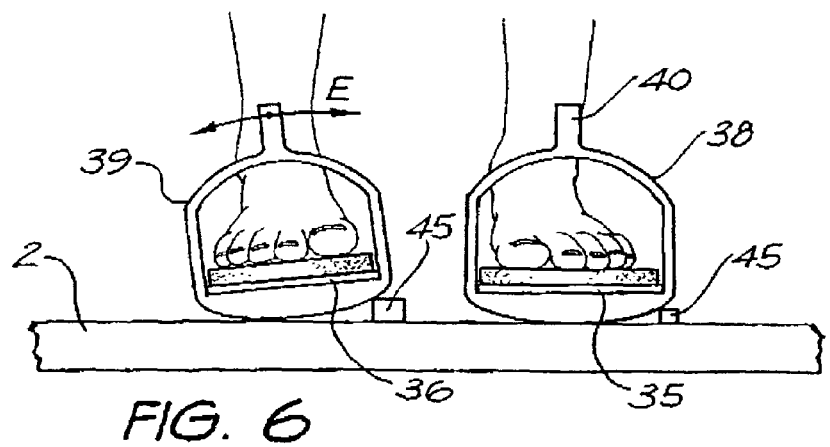
FIG. 6 is a front elevation showing the movement of the stirrups.
Figure 7:
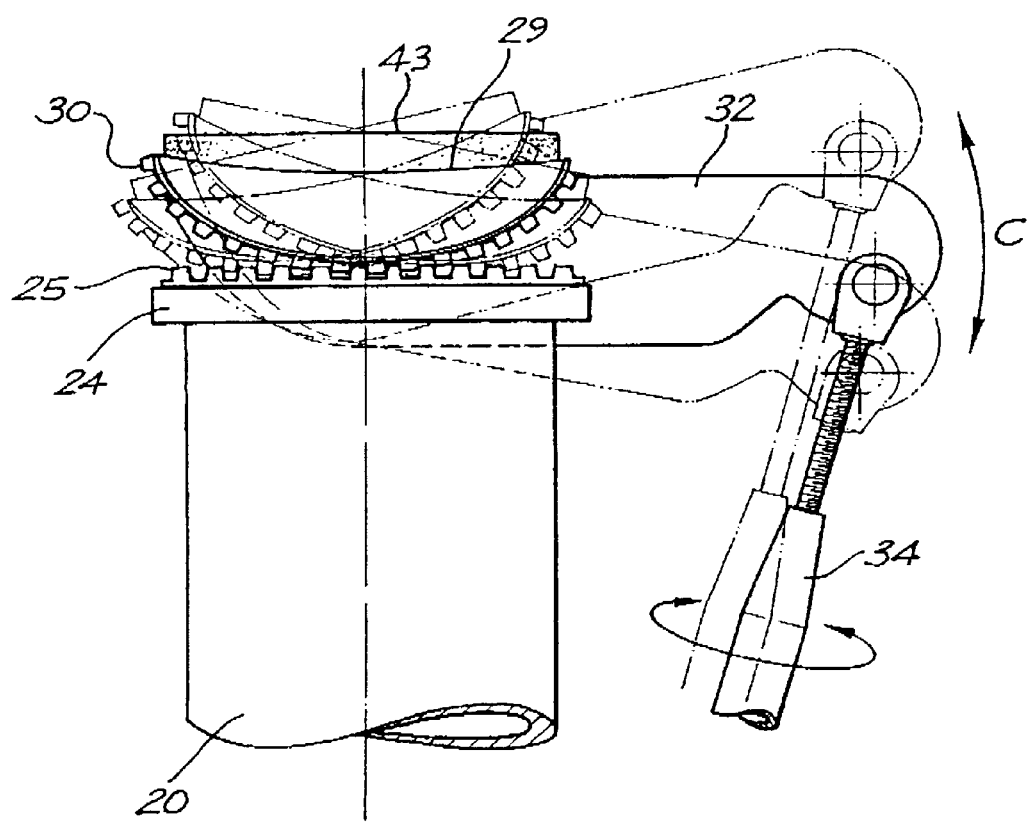
FIG. 7 is an enlarged rear elevation showing the movement of the right heel support and its associated tilt lever arm.

The podiatrist is then able to examine the bone formation of the client and, in particular, whether the orientation of the heel whilst standing is substantially vertical so as to properly transmit the forces generated by walking, running, etc. If, for example, the right heel is out of vertical (pronation or supination), then the podiatrist is able to adjust the turn buckle 34 as indicated in FIG. 7 so as to raise or lower the tilt arm lever 32. As indicated in FIG. 7 this simultaneously both rotates the heel support 29 about the heel-toe axis of the patient's foot, and also translates the heel support 28 transversely to that axis because of the inter-engagement of the teeth on the racks 25, 30. In this way, the heel support 29 can be adjusted by the podiatrist to correct any malalignment of the patient's right heel. In the course of this adjustment, the right foot of the patient is normally twisted to a certain extent and this generally throws the front portion (forefoot) of the patient's foot out of the desired alignment. As indicated in FIG. 6, the stirrup 39 is now able to be moved in the directions indicated by arrow E in FIG. 6. This has two effects, firstly to rotate the front portion of the patient's foot so as to correct any malalignment and secondly to move the stirrups 39 transverse to the heel-toe axis as necessary. This movement is performed manually by the podiatrist grasping the corresponding lug 40. Once the correct orientation for the forefoot is achieved the stirrup 39 is held in position by means of a block 45 as seen in FIG. 6. As also seen in FIG. 6, each stirrup 39 has a curved bottom surface which is able to both pivot and slide over the bench top 2. The upper surface of the stirrup bottom is flat to receive the corresponding foot plate 35, 36.

Since the patient 6 is standing in front of the mirror 3 while the apparatus is used to correctly align the patient's feet, the patient can therefore immediately see that their feet—and hence their legs and the rest of their body—are correctly aligned. Usually the patient will feel an immediate sense of "standing straight" and is able to voice any comfort concerns to the podiatrist as they emerge.

Figure 8:
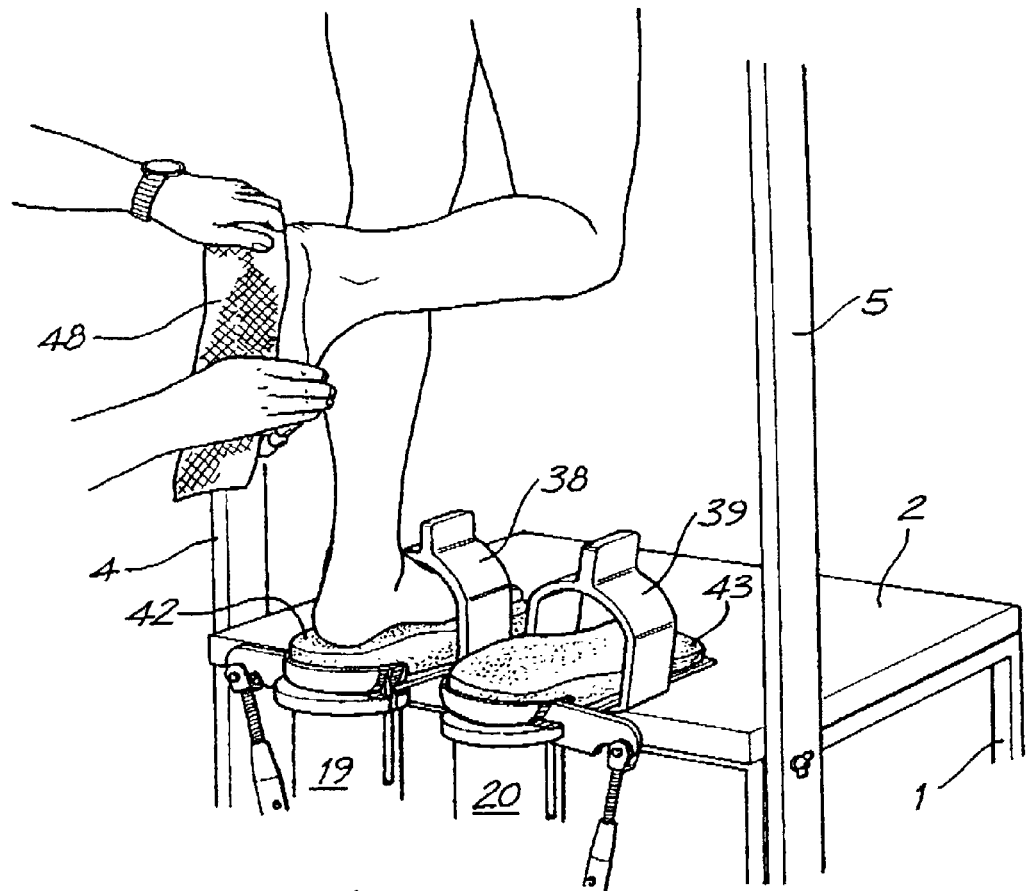
FIG. 8 is a rear perspective view similar to FIG. 1 but illustrating the application of a casting bandage.

Once this procedure is complete, the patient's stance, as regards the right foot, is effectively corrected. The identical procedure is then carried out, as necessary, for the left foot so that the patient's stance is fully corrected for both feet. Then, as indicated in FIG. 8, the right foot is moved rearwardly and lifted into the position illustrated in FIG. 8 at which stage the podiatrist applies a fabric bandage 48 which is impregnated with plaster-of-paris, or similar, and is then dipped in water. This constitutes a casting material. With the wet casting bandage 48 adhering to the patient's right foot by atmospheric pressure, all air having been forced out between the foot and the bandage 48, the right foot is then returned to its previous position and the patient's weight re-exerted on the liner 43.

The identical procedure is then carried out on the left foot and the podiatrist checks the settings of the heel supports 28, 29 and stirrups 38, 39 to ensure that the adjustment of the patient's stance is correct and complete. The patient then maintains this stance until the casting material has set. Typical setting times are in the range of 1–3 minutes.

Alternatively, if the podiatrist is sufficiently quick in the adjustments required, the bandage 48 can be applied initially and all adjustments made with the bandage 48 in-situ.

Figure 9:
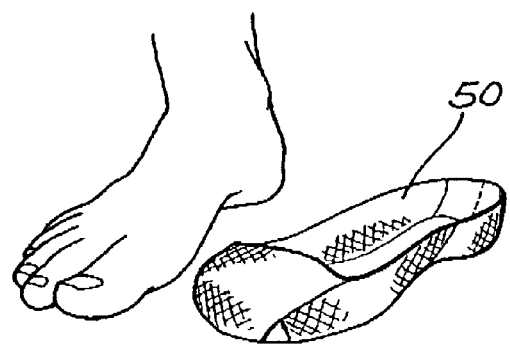
FIG. 9 illustrates the final cast negative taken from the patient's foot.

Preferably, the podiatrist uses a vertically aligned pencil holder 52 (illustrated in FIG. 4 and omitted from FIGS. 1–3 and 5, 7 and 8 for clarity) in order to make a vertical mark (indicated by a broken line in FIG. 9) down the outside rear of the cast 50. Each of the supports 19, 20 is provided with a corresponding holder 50 which is able to receive a pencil or marker pen (FIG. 4) and is able to slide vertically in the direction indicated by arrow F in FIG. 4. The vertical line on the cast 50 provides a useful reference for subsequent casting operations.

Thereafter, the patient raises the right leg into the position illustrated in FIG. 8 and the set cast 50 (FIG. 9) is able to be removed from his foot in the same way that one removes a slipper or slip-on shoe. Then the completed cast 50 for the left foot is similarly removed and the patient steps down from the apparatus.

The completed cast 50 forms a negative cast of the patient's foot in its fully compensated position whilst bearing the patient's weight. Thus the spreading of the tissue of the foot due to the application of the patient's weight is taken account of exactly in the casting procedure. The desired result of a cast of the patient's corrected and weight bearing foot has been achieved.

Thereafter, the cast 40 can be used as a mould to produce a mould of the patient's foot in the compensated and load bearing position. An orthotic innersole or insole is then able to be prepared from the cast of the patient's foot in conventional fashion.

Because the casts are fabricated while the feet are in the correct position, rather than being held in the air with the position "replicated", guesswork and human error are effectively removed from the process. Unskilled labour can subsequently be used in the laboratory where the orthoses are made, and the chances of the patient being satisfied with the end product are increased.

Production time is also decreased and there is less likelihood a patient will have to return orthoses to be remade because the patient is dissatisfied with the devices.

The foregoing describes only one embodiment of the present invention and modifications, obvious to those skilled in the art, can be made thereto without departing from the scope of the present invention. For example, the liners 42, 43 are preferably provided in three sizes; large, medium and small to allow for feet of different sizes.

Furthermore, the liners 42, 43 can be replaced by pressure sensitive pads, known per se, from which the measurements of pressure at various points can be taken and an orthotic device created from such measurements in known fashion. U.S. Pat. No. 5,088,503 (Seitz) is indicative of the known art in this area.

In an alternative arrangement, the orthotic insole can be produced directly on the apparatus instead of using the plaster cast 50 as a intermediate medium. U.S. Pat. No. 4,747,989 (Peterson) is indicative of the known art in this area. Essentially a thermally softenable plastics material such as polypropylene is heated to soften it. If desired a thin, thermally insulative sheet can be located above the softened plastics (to protect the patient's foot from burning). The heated material is then placed on the corresponding liner 42, 43. Then the adjustments required for the patient are carried out. Finally the plastics material is allowed to cool and naturally adopts the desired shape of the orthotic innersole.

The term "comprising" as used herein is used in the inclusive sense of "having" or "including" and not in the exclusive sense of "consisting only of".

The invention claimed is:

1. Apparatus to correctly align a foot to permit an orthotic device to be fabricated, said apparatus comprising:
   a heel support and a front foot rest positioned substantially level therewith and in front of the heel support to define a heel-toe axis in front of the heel support, said heel support being mounted on a heel adjustment means arranged to simultaneously pivot said heel support about said heel-toe axis and move said heel support in a direction transverse to said heel-toe axis, and
   a front foot support located on said front foot rest and able to be both rotated about said heel-toe axis and moved in a direction transverse to said heel-toe axis,
   wherein said front foot support comprises a stirrup having an appreciable extent in the direction of said heel-toe axis.

2. Apparatus as claimed in claim 1, wherein a foot plate extends between said heel support and said front foot rest and is located within said front foot support.

3. Apparatus as claimed in claim 1, wherein a deformable liner shaped to support the plantar surface of a patient's foot extends from said heel support through said front foot support.

4. Apparatus as claimed in claim 1, wherein said heel adjustment means comprises a vertically extending support having a substantially flat top over which a substantially flat rack extends, a curved rack formed on said heel support and engaged with said flat rack, and a tilt lever arm extending from said heel support and tiltable to change the point of inter-engagement of said flat and curved racks.

5. Apparatus as claimed in claim 4, wherein a turnbuckle interconnects said tilt lever arm and a base of said vertically extending support.

6. Apparatus as claimed in claim 5, wherein said tilt lever arm extends from the underside of said heel support, has a substantial vertical extent, and is carried in a slot in said flat top, the inter-engagement of said tilt lever arm and slot substantially preventing movement of said heel support in the direction of said heel-toe axis.

7. Apparatus as claimed in claim 4, wherein said vertically extending support is rotatable about the vertical axis and releasably clampable in relation thereto to permit toe-in or toe-out adjustment of said heel-toe axis.

8. Apparatus as claimed in claim 4 and having a pair of said heel supports and translation means to adjust the relative distance between said heel supports in a direction substantially transverse to the heel-toe axes.

9. A method of casting a mould of a compensated foot whilst a patient's weight is carried by the foot, said method comprising the steps of:
   a. standing the patient on a pair of spaced apart heel supports whilst supporting the front of the patient's feet,
   b. adjusting at least the heel supports to compensate for any malalignment of the patient's feet,
   c. lifting one foot free of said heel support and applying a settable casting bandage to said foot,
   d. replacing said one foot on said heel support and, if necessary, repeating said compensation step (b),
   e. maintaining said foot in the compensated configuration until said casting bandage sets, and
   f. removing said one foot from said heel support and slipping said one foot from said set cast.

10. A method of casting a mould of a compensated foot whilst a patient's weight is carried by the foot, said method comprising the steps of:
   a. standing the patient on a pair of spaced apart heel supports whilst supporting the front of the patient's feet,
   b. lifting one foot free of said heel support and applying a settable casting bandage to said foot,
   c. replacing said one foot on said heel support,
   d. adjusting at least the heel supports to compensate for any malalignment of the patient's feet,
   e. maintaining said foot in the compensated configuration until said casting bandage sets, and
   f. removing said one foot from said heel support and slipping said one foot from said set cast.

11. The method as claimed in claim 9, wherein said adjusting step includes the simultaneous pivoting of at least one said heel supports about a heel-toe axis of said foot and movement of said heel support transverse to said heel-toe axis.

12. The method as claimed in claim 11, wherein said adjusting step includes the additional step of adjusting the patient's forefoot by rotation thereof about said heel-toe axis and simultaneous movement substantially transverse to said heel-toe axis.

13. The method as claimed in claim 9 including the further step of:
   g. placing a deformable liner on each of said heel supports prior to carrying out step (a).

14. The method as claimed in claim 9 and carried out for both feet of said patient in turn to thereby create two said casts.

15. Apparatus to correctly align a foot to permit an orthotic device to be fabricated, said apparatus comprising:
   a heel support and a front foot rest positioned substantially level therewith and in front of the heel support to define a heel-toe axis in front of the heel support, said heel support being mounted on a heel adjustment means arranged to simultaneously pivot said heel support about said heel-toe axis and move said heel support in a direction transverse to said heel-toe axis,
   wherein said heel adjustment means comprises a vertically extending support having a substantially flat top over which a substantially flat rack extends, a curved rack formed on said heel support and engaged with said flat rack, and a tilt lever arm extending from said heel support and tiltable to change the point of inter-engagement of said flat and curved racks.

16. Apparatus as claimed in claim 15, wherein a turnbuckle interconnects said tilt lever arm and a base of said vertically extending support.

* * * * *